(12) United States Patent
Mihalik et al.

(10) Patent No.: US 6,537,985 B1
(45) Date of Patent: Mar. 25, 2003

(54) ANTIBIOTIC FORMULATION AND A METHOD OF MAKING THIS FORMULATION

(75) Inventors: Richard Mihalik, St. Joseph, MO (US); John R. Carpenter, Savannah, MO (US); Heidi M. P. Faris, Webster City, IA (US)

(73) Assignee: Phoenix Scientific, Inc., St. Joseph, MO (US)

( * ) Notice: Subject to any disclaimer, the term of this patent is extended or adjusted under 35 U.S.C. 154(b) by 0 days.

(21) Appl. No.: 09/997,978

(22) Filed: Nov. 30, 2001

(51) Int. Cl.$^7$ ............................................. A61K 31/545
(52) U.S. Cl. ...................... 514/200; 514/198; 514/199
(58) Field of Search ................................. 514/198, 199, 514/200

(56) References Cited

U.S. PATENT DOCUMENTS

| | | | | |
|---|---|---|---|---|
| 4,560,553 A | * | 12/1985 | Zupan | 424/78 |
| 4,960,771 A | * | 10/1990 | Rajadhyaksha | 514/228.8 |
| 5,032,402 A | * | 7/1991 | Digenis et al. | 424/448 |
| 5,409,917 A | * | 4/1995 | Robinson et al. | 514/200 |
| 5,747,058 A | * | 5/1998 | Tipton et al. | 424/423 |
| 5,780,044 A | * | 7/1998 | Yewey et al. | 424/426 |
| 5,945,115 A | * | 8/1999 | Dunn et al. | 424/422 |
| 6,143,314 A | * | 11/2000 | Chandrashekar et al. | 424/426 |

* cited by examiner

Primary Examiner—James H. Reamer
(74) Attorney, Agent, or Firm—Stinson Morrison Hecker LLP

(57) ABSTRACT

An antibiotic formulation in a true solution is provided. This formulation includes an antibiotic and N-methyl-2-pyrrolidone. It also may include a preservative, an antioxidant, and/or an additive. The antibiotic is a beta lactam, such as a penicillin, a cephalosporin, other beta lactams, or combinations thereof. The formulation is made by dissolving the antibiotic in the N-methyl-2-pyrrolidone. The antibiotic formulation is suitable for use at temperatures below about 0° C. and without agitation. Further, the antibiotic formulation in true solution can be made with non-sterile ingredients and can be filtered to remove impurities.

20 Claims, No Drawings

ANTIBIOTIC FORMULATION AND A METHOD OF MAKING THIS FORMULATION

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

The present invention relates to an antibiotic formulation. More specifically, the present invention relates to an antibiotic formulation that includes beta lactams in a true solution.

Historically, beta lactams are insoluble. Current formulations of beta lactams are sterile suspensions or sterile powders for suspension of corresponding salts. The sterile powder for suspension becomes a solution with the addition of diluents such as sterile water or saline.

One disadvantage associated with antibiotic drugs in sterile suspension formulations or sterile powders for suspension is that they cannot be filtered for sterility. If a suspension were filtered to remove impurities, the active pharmaceutical ingredient would be filtered out of the formulation and render the product inactive for its intended use.

A second disadvantage associated with antibiotic drugs in a suspension formulation is that sterile ingredients must be used in making the formulation. This is disadvantageous because sterile ingredients are more costly than non-sterile components. Also, using sterile ingredients makes the process for making the formulation time-consuming and labor intensive.

A third disadvantage associated with antibiotic drugs in suspension formulations is that uniform dosages are not necessarily obtained from such formulations because they may not deliver a constant, uniform amount of drug and liquid.

A fourth disadvantage associated with antibiotic drugs in suspension formulations is that the suspensions are both a solid and a liquid. Thus, solids settle out and fall to the bottom of the container over time. They become re-suspended only after agitation. In addition, over time solids can aggregate as a result of compaction and/or re-crystallization due to temperature fluctuations.

Further, a typical suspension diluent is sterile water, sterile saline or other sterile medium, which may freeze at temperatures below 0° C. Therefore, an antibiotic in a sterile suspension must be warmed before administration when temperatures are below freezing.

In order to overcome these disadvantages, an antibiotic formulation in a true solution is needed.

SUMMARY OF THE INVENTION

It is an object of the present invention to provide an antibiotic formulation that is in a true solution so that it does not separate into solid and liquid components.

It is a further object of the present invention to provide a method of making an antibiotic formulation in true solution so that it may be filtered without removing the active ingredient.

It is yet another object of the present invention to provide an antibiotic formulation that can be administered without agitation so that it can be administered more quickly and easily.

Still another object of the present invention is to provide a method of making an antibiotic formulation using non-sterile manufacturing materials so as to save manufacturing time and costs.

It is another object of the present invention to provide an antibiotic formulation that can be administered without warming when temperatures are below freezing so that it can be administered more quickly and easily.

According to the present invention, the foregoing and other objects are achieved by an antibiotic formulation in a true solution. This formulation includes an antibiotic and N-methyl-2-pyrrolidone. It may also include an antioxidant, a preservative and/or an additive. The antibiotic is a beta lactam, such as a penicillin, a cephalosporin, other beta lactams, or combinations thereof. The formulation is made by dissolving the antibiotic in the N-methyl-2-pyrrolidone. The antibiotic formulation is suitable for use at temperatures below freezing and without agitation.

Additional objects, advantages and novel features of the invention will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF THE PREFERRED EMBODIMENTS

The formulation of the present invention is an antibiotic in a true solution. This formulation includes an antibiotic and a solvent. Optionally, a preservative, an antioxidant, and/or an additive may be added to the formulation.

The antibiotic used in the formulation is a beta lactam, such as a penicillin, a cephalosporin, other beta lactams, or combinations thereof. The penicillins that can be used in the formulation of the present invention include, but are not limited to, procaine penicillin G, benzathine penicillin G, amoxicillin, ampicillin, carbenicillin, piperacillin, ticarcillin, or combinations thereof The cephalosporins that can be used in the formulation of the present invention include, but are not limited to, ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cloxacillin, or combinations thereof. Preferably, if a cephalosporin is included, ceftiofur sodium is used. Other beta lactams that can be used in the formulation include, but are not limited to, aztreonam, cefotetan, loracarbef, cefoxitin, meropenem, imipenem, or combinations thereof.

The solvent used in the formulation of the present invention is a pyrrolidone solvent, namely, N-methyl-2-pyrrolidone (NM2P).

It is desirable to add a preservative to the formulation of the present invention. The preservative that may be used in the formulation of the present invention can be, but is not limited to, benzyl alcohol, ethyl alcohol, parabens such as methyl, ethyl and/or propylparaben, chlorobutanol, sodium benzoate, benzoic acid, myristyl-gamma-picolinium chloride, benzathonium chloride, or combinations thereof. Preferably, benzyl alcohol is used if a preservative is used in the formulation. Preferably, a preservative is added to the formulation if a beta lactam is used as the antibiotic in the formulation.

The antioxidant that may be used in the formulation of the present invention can be, but is not limited to, edetate disodium, sodium metabisulfite, sodium formaldehyde sulfoxylate, vitamin E acetate, vitamin C, vitamin $B_{12}$ or combinations thereof.

The additive that may be used in the formulation of the present invention can be, but is not limited to, 2-pyrrolidone, N-5-dimethyl-2-pyrrolidone, 3-3-dimethyl-2-pyrrolidone, N-ethyl-2-pyrrolidone, N-ethyloxy-2-pyrrolidone, N-ethylene-2-pyrrolidone, pyrrolidone, glycerol formal, propylene glycol, polyethylene glycol, glycerine, water, and combinations thereof.

The antibiotic formulation is made by first warming the N-methyl-2-pyrrolidone. Preferably, the NM2P is warmed to about 30–50° C. Most preferably, the NM2P is warmed to about 35–45° C. The antibiotic is added to the NM2P, and the mixture is stirred until the antibiotic dissolves. The mixture is then cooled. Preferably, it is cooled to at least about 30° C. A preservative, antioxidant, and/or additive may then be added to the mixture, and the mixture is stirred. Additional NM2P may be added to further dilute the formulation, if desired, or to fully dissolve the antibiotic.

The antibiotic is about 5–50% by weight of the true solution. Preferably, it is about 15–40% by weight of the true solution. Most preferably, it is about 20–30% by weight of the true solution.

The total amount of preservative in this formulation is about 0–15% weight per volume of the solution (w/v). Preferably, a preservative is present in an amount of about 0.02–10% w/v. Most preferably, a preservative is about 0.5–3% w/v of the formulation. If included, the antioxidant is about 0.5–10% w/v of the solution. If included, preferably, the antioxidant is about 1–5% by w/v of the solution.

The antibiotic formulation of the present invention is a true solution. Therefore, it can be formulated from non-sterile manufacturing materials and can be filtered to remove contaminants.

In addition, by being a true solution, it is more readily available and quickly absorbed. Therefore, it is more quickly available to enter tissues and be biologically available. In contrast, biological absorption from suspensions of the prior art is dependent upon drug particle size. The true solution of the present invention removes the potential problem of particle size variation.

Further, the antibiotic formulation of the present invention can be administered to a target species below about 0° C. In fact, it does not freeze until it is at temperatures below about −20° C. Still further, the antibiotic formulation of the present invention can be administered without being agitated before use.

It is specifically contemplated that this formulation can be administered to animals including, but are not limited to, bovines, ovines, porcines, felines, canines and/or ungulates. For this reason, it is especially useful that the formulation easily can be administered at cold temperatures so as to treat animals that are outside in the winter. The formulation can be administered orally, parenterally, or topically.

The following are examples of the antibiotic formulation of the present invention and methods of making these formulations. Examples 1–3 illustrate making an antibiotic formulation with beta lactams in a true solution. Example 4 illustrates making a cephalosporin formulation in a true solution. These examples are not meant in any way to limit the scope of this invention.

EXAMPLE 1

The formulation of the present invention was made as follows: 330 milliliters of N-methyl-2-pyrrolidone (NM2P) were placed in a dry container at an initial temperature of 19° C. The NM2P was warmed to 35–40° C. 125 grams of the antibiotic amoxicillin in powder form were added. The mixture was stirred until most of the material was dissolved resulting in a lemon-yellow solution. The mixture was cooled to 30° C. After cooling the mixture to 30° C., approximately 15 grams of the preservative benzyl alcohol were added to the mixture. Following this, approximately 217 grams of NM2P were added to the mixture. The temperature was then increased up to 50° C. as necessary to dissolve the antibiotic completely.

EXAMPLE 2

The formulation of the present invention was made as follows: Approximately 300 milliliters of N-methyl-2-pyrrolidone (NM2P) were placed in a dry container. The NM2P was warmed to 35–40° C. Approximately 75 grams of activity of the antibiotic of penicillin G procaine and 75 grams of activity of penicillin G benzathine were added to NM2P. The mixture was mixed for 1 hour to produce a milky off-white to straw yellow opaque suspension. The mixture was cooled to 25–30° C. After cooling the mixture, approximately 7.5 grams of the preservative benzyl alcohol were added to the mixture. The mixture was diluted to 500 milliliters with NM2P. The mixture was stirred until all of the powder dissolved so as to result in a clear, straw-yellow solution.

EXAMPLE 3

The formulation of the present invention was made as follows: Approximately 300 milliliters of N-methyl-2-pyrrolidone (NM2P) were placed in a dry container. The NM2P was warmed to 35–40° C. Approximately 150 grams of activity of penicillin G procaine were added to the NM2P. The mixture was stirred for 13 minutes until the powder was completely dissolved to produce a light straw-colored clear solution. The mixture was cooled to 25–30° C. After cooling the mixture, approximately 7.5 grams of the preservative benzyl alcohol were added to the mixture. The mixture was diluted with NM2P to 500 milliliters, and the solution remained a clear, straw-yellow solution.

EXAMPLE 4

The formulation of the present invention was made as follows: Approximately 1 gram of ceftiofur was obtained in a lyophilized form as the sodium salt was mixed with sodium hydroxide and potassium phosphate. Approximately 4 milliliters of N-methyl-2-pyrrolidone were added to the ceftiofur sodium. The mixture was mixed to completely dissolve the components. The resulting solution contained approximately 25% by weight ceftiofur sodium in a true solution.

From the foregoing, it will be seen that this invention is one well adapted to attain all the ends and objects hereinabove set forth together with other advantages which are obvious and inherent to the formulation. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. An antibiotic formulation, comprising a mixture of:
   at least one beta lactam antibiotic; and
   N-methyl-2-pyrrolidone, wherein said antibiotic is dissolved in said N-methyl-2-pyrrolidone to form said antibiotic formulation and wherein said formulation is a true solution.

2. The formulation of claim 1, wherein said beta lactam is selected from the group consisting of a penicillin, a cephalosporin, aztreonam, cefotetan, loracarbef, cefoxitin, meropenem, imipenem, and combinations thereof.

3. The formulation of claim 2, wherein said beta lactam is a penicillin selected from the group consisting of procaine penicillin G, benzathine penicillin G, amoxicillin, ampicillin, carbenicillin, piperacillin, ticarcillin, and combinations thereof.

4. The formulation of claim 2, wherein said beta lactam is a cephalosporin selected from the group consisting of ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cloxacillin, and combinations thereof.

5. The formulation of claim 1, further comprising:
   at least one preservative.

6. The formulation of claim 5, wherein said preservative is selected from the group consisting of benzyl alcohol, ethyl alcohol, parabens, chlorobutanol, sodium benzoate, benzoic acid, myristyl-gamma picolinium chloride, and combinations thereof.

7. The formulation of claim 1, further comprising:
   an antioxidant.

8. The formulation of claim 7, wherein said antioxidant is selected from the group consisting of edetate disodium, sodium metabisulfite, sodium formaldehyde sulfoxylate, vitamin E acetate, vitamin C, vitamin $B_{12}$, and combinations thereof.

9. The formulation of claim 1, further comprising:
   an additive.

10. The formulation of claim 9, where said additive is selected from the group consisting of water, 2-pyrrolidone, N-5-dimethyl-2-pyrrolidone, 3-3-dimethyl-2-pyrrolidone, N-ethyl-2-pyrrolidone, N-ethyloxy-2-pyrrolidone, N-ethylene-2-pyrrolidone, pyrrolidone, glycerol formal, propylene glycol, polyethylene glycol, glycerine, and combinations thereof.

11. The method of claim 1, wherein said antibiotic is about 5–50% w/v of said formulation.

12. The method of claim 11, wherein said antibiotic is about 15–40% w/v of said formulation.

13. A method of making an antibiotic formulation, comprising:
   providing N-methyl-2 pyrrolidone;
   providing a beta lactam antibiotic;
   adding said antibiotic to said N-methyl-2-pyrrolidone; and
   mixing N-methyl-2-pyrrolidone and said antibiotic so as to dissolve said antibiotic and form an antibiotic formulation that is a true solution.

14. A method of claim 13, further comprising:
   adding at least one preservative to said formulation.

15. A method of claim 13, further comprising:
   adding an antioxidant to said formulation.

16. A method of claim 13, further comprising:
   adding an additive selected from the group consisting of water, 2-pyrrolidone, N-5-dimethyl-2-pyrrolidone, 3-3-dimethyl-2-pyrrolidone, N-ethyl-2-pyrrolidone, N-ethyloxy-2-pyrrolidone, N-ethylene-2-pyrrolidone, pyrrolidone, glycerol formal, propylene glycol, polyethylene glycol, glycerine, and combinations thereof to said formulation.

17. The method of claim 13, further comprising:
   warming said N-methyl-2-pyrrolidone to about 35–50° C. before adding said antibiotic.

18. The method of claim 17, further comprising:
   cooling said antibiotic formulation to about 30° C. after said mixing step.

19. An antibiotic formulation, comprising a mixture of:
   a beta lactam antibiotic;
   a preservative selected from the group consisting of benzyl alcohol, ethyl alcohol, parabens, chlorobutanol, sodium benzoate, benzoic acid, myristyl-gamma picolinium chloride, and combinations thereof;
   an antioxidant selected from the group consisting of edetate disodium, sodium metabisulfite, sodium formaldehyde sulfoxylate, vitamin E acetate, vitamin C, vitamin $B_{12}$, and combinations thereof; and
   N-methyl-2-pyrrolidone, wherein said antibiotic is dissolved in said N-methyl-2-pyrrolidone to form said antibiotic formulation and wherein said formulation is a true solution.

20. The formulation of claim 19, further comprising:
   an additive selected from the group consisting of 2-pyrrolidone, N-5-dimethyl-2-pyrrolidone, 3-3-dimethyl-2-pyrrolidone, N-ethyl-2-pyrrolidone, N-ethyloxy-2-pyrrolidone, N-ethylene-2-pyrrolidone, pyrrolidone, glycerol formal, propylene glycol, polyethylene glycol, glycerine, water, and combinations thereof.

* * * * *